US006780601B2

(12) United States Patent
Wang et al.

(10) Patent No.: US 6,780,601 B2
(45) Date of Patent: Aug. 24, 2004

(54) METHOD OF IDENTIFYING AN AGENT THAT MODULATES THE ACTIVITY OF A LEPIDOPTERAN GLUTAMATE-GATED CHLORIDE CHANNEL

(75) Inventors: Xiao-Zhuo Michelle Wang, Chapel Hill, NC (US); Xavier Georges Sarda, Sainte Genevieve des Bois (FR); Michael David Tomalski, Raleigh, NC (US); Vincent Paul Mary Wingate, Chapel Hill, NC (US)

(73) Assignee: Aventis CropScience SA, Lyons (FR)

( * ) Notice: Subject to any disclaimer, the term of this patent is extended or adjusted under 35 U.S.C. 154(b) by 85 days.

(21) Appl. No.: 09/969,844

(22) Filed: Oct. 3, 2001

(65) Prior Publication Data

US 2002/0192776 A1 Dec. 19, 2002

Related U.S. Application Data

(62) Division of application No. 09/592,891, filed on Jun. 13, 2000, now Pat. No. 6,329,174.

(51) Int. Cl.$^7$ ........................ G01N 33/53; G01N 33/567
(52) U.S. Cl. ........................ 435/7.1; 435/7.2; 435/7.21
(58) Field of Search ........................ 435/7.1, 7.2, 7.21

(56) References Cited

U.S. PATENT DOCUMENTS

| | | | |
|---|---|---|---|
| 5,527,703 A | 6/1996 | Cully et al. | |
| 5,693,492 A | 12/1997 | Cully et al. | |

FOREIGN PATENT DOCUMENTS

| | | |
|---|---|---|
| WO | 9849185 | 5/1998 |
| WO | 9907828 | 2/1999 |

OTHER PUBLICATIONS

Arena et al. (1991) "Avermectin–Sensitive Chloride Currents Induced by *Caenorhabditis Elegans* RNA in Xenopus Oocytes," Molecular Pharm. 40:368.

Arena et al. (1992) "Expression of a Glutamate–Activated Chloride Current in *Xenopus* Oocytes Injected with *Caenorhabditis Elegans* RNA: Evidence for Modulation by Avermectin," Molecular–Brain Research 15:339.

Cully et al. (1994) "Cloning of an Avermectin–Sensitive Glutamate–Gated Cholride Channel from *Caenorhabditis Elegans*," Nature 371:707.

Cully et al. (1996) "Identification of a *Drosophila Melanogaster* Glutamate–Gated Chloride Channel Sensitive to the Antiparasitic Agent Avermectin," J. Biol. Chem. 271:20187.

Delany et al. (1998) "Cloning and Localisation of an Avermectin Receptor–Related Subunit from *Haemonchus Contortus*," Mol. Biochem. Parasit., 97:177.

Mikayama et al. (1993) "molecular Cloning and Functional Expression of a cDNA Encoding Glycosylation–Inhibitin Factor," Proc. Natl. Acad. Sci. USA 90:10056.

Voet et al. (1990) Biochemistry, John Wiley & Sons, Inc., 126–128 and 228–234.

Smith MH, Warren VA, Thomas BS, Brochu RM, Ertel EA, Rohrer S, Schaeffer J, Schmatz D, Petuch BR, Tang YS, Meinke PT, Kaczorowski GJ, Cohen CJ. Nodulisporic acid opens insect glutamate–gated chloride channels: identification of a new high affinity modulator. Biochemistry 2000;39:5543–5554.

Pomes A, Kempner E, Rohrer S. Target size analysis of an avermectin binding site from *Drosophila melanogaster*. Biochimica et Biophysica Acta 1997;1339:233–238.

Yu SJ, Nguyen SN. Insecticide susceptibility and detoxification enzyme activities in permethrin–selected diamondback moths. Peticide Biochemistry and Physiology 1996;56:69–77.

*Primary Examiner*—Prema Mertz
(74) *Attorney, Agent, or Firm*—Baker Botts L.L.P.

(57) ABSTRACT

The present invention is directed to a nucleic acid encoding a lepidopteran glutamate-gated chloride channel. Vectors and host cells comprising the nucleic acid are also provided. A method of identifying agents that modulate the activity of a lepidopteran glutamate-gated chloride channel is also provided. Such agents are useful as insecticides.

1 Claim, 1 Drawing Sheet

METHOD OF IDENTIFYING AN AGENT THAT MODULATES THE ACTIVITY OF A LEPIDOPTERAN GLUTAMATE-GATED CHLORIDE CHANNEL

SPECIFICATION

This is a divisional of application Ser. No. 09/592,891 filed Jun. 13, 2000, now U.S. Pat. No. 6,329,174.

BACKGROUND OF THE INVENTION

Glutamate-gated chloride channels are a family of ligand-gated chloride channels unique to invertebrates. Glutamate-gated chloride channels have been cloned from *Caenorhabditis elegans* (Cully et al. (1994) Nature 20:371; U.S. Pat. No. 5,527,703), *Drosophila melanogaster* (Cully et al. (1996) J. Biol. Chem. 271:20187 and U.S. Pat. No. 5,693,492), *Haemonchus contortus* (Delany et al. (1998) Mol. Biochem. Parasit. 97:177), *Lucilia cuprina* (GenBank Accession No. AAC31949) and *Schistocerca americana* (Cohen et al. (1999) 29th Annual Neuroscience Meeting, p. 199). The clones isolated from *C. elegans, D. melanogaster* and *S. americana* have been functionally expressed in Xenopus oocytes, and shown to be activated by glutamate and avermectin. (Arena et al. (1991) Molecular Pharm. 40:368; Arena et al. (1992) Molecular Brain Research 15:339; U.S. Pat. No. 5,693,492; U.S. Pat. No. 5,527,703; Cohen et al., supra).

Because glutamate-gated chloride channels are specific to invertebrates, the channels provide a target for insecticides. In particular, the glutamate-gated chloride channels are the target of the avermectin class of insecticides. Avermectins are naturally occurring and synthetic macrocylic lactones that are widely used in the treatment of parasites and insects.

Insects of the order lepidoptera are significant pests, and in particular the larvae are destructive defoliaters. Further, lepidopteran pests are typically harder to control than diptera. Accordingly, there is a need to identify and develop safe and specific insecticides against lepidopteran pests. The present invention addresses this need by providing isolated nucleic acids encoding a lepidopteran glutamate-gated chloride channel, recombinant lepidopteran glutamate-gated chloride channels, and a method of identifying agents that modulate the activity of the channel.

SUMMARY OF THE INVENTION

The present invention is directed to an isolated nucleic acid encoding a lepidopteran glutamate-gated chloride channel. In a preferred embodiment the nucleic acid is isolatable from *Heliothis virescens*. In another preferred embodiment the nucleic acid comprises a sequence encoding the amino acid sequence of SEQ ID NO. 14.

The present invention further comprises vectors comprising a nucleic acid encoding a lepidopteran glutamate-gated chloride channel, and host cells comprising the vectors.

Another aspect of the present invention provides a recombinant lepidopteran glutamate-gated chloride channel, and kits and compositions comprising a recombinant lepidopteran glutamate-gated chloride channel. A method for preparing a lepidopteran glutamate-gated chloride channel is also provided.

In yet another embodiment, the present invention provides a Xenopus oocyte comprising a nucleic acid encoding a lepidopteran glutamate-gated chloride channel, and a Xenopus occyte expressing a functional lepidopteran glutamate-gated chloride channel.

The present invention further provides a method of identifying agents that modulate the activity of the lepidopteran glutamate-gated chloride channel, and agents identified by the method.

DETAILED DESCRIPTION OF THE INVENTION

Figure 1:
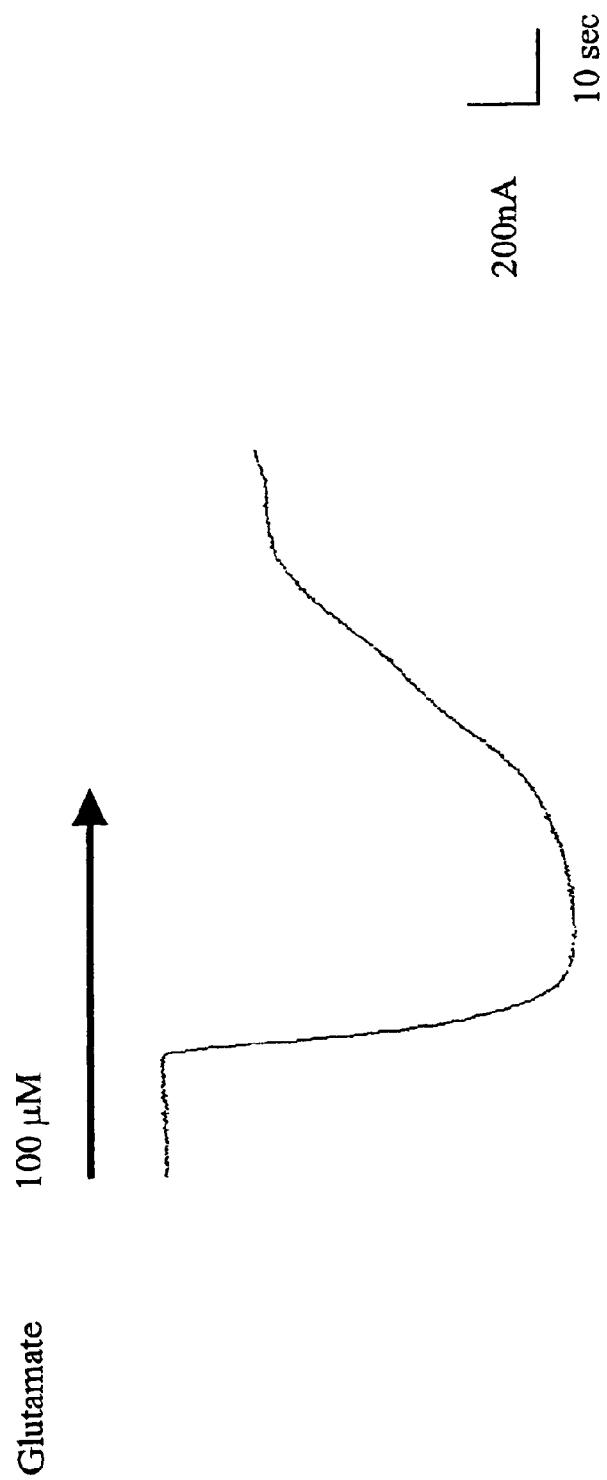
FIG. 1 presents electrophysiological recordings demonstrating the effect of glutamate on a lepidopteran glutamate-gated chloride channel expressed in oocytes.

The present invention is directed to isolated nucleic acids encoding lepidopteran glutamate-gated chloride channels. An isolated nucleic acid encoding a lepidopteran glutamate gated chloride channel is defined herein as a nucleic acid isolatable from an insect of the order lepidoptera and capable of encoding a functional glutamate-gated chloride channel. In a preferred embodiment, the nucleic acid is isolatable from Heliothis. In a more preferred embodiment, the nucleic acid is isolatable from *Heliothis virescens*. A functional glutamate-gated chloride channel is defined herein as a protein having the ability to bind glutamate and thereby mediate chloride flux in a cell expressing the channel.

The isolated nucleic acid may be DNA or RNA, including cDNA and mRNA. In a preferred embodiment, the isolated nucleic acid has a sequence encoding the amino acid sequence at of SEQ ID NO. 14. The ordinarily skilled artisan, with knowledge of the genetic code, can determine DNA and RNA sequences that encode the amino acid sequence set forth in SEQ ID NO. 14. Further, the sequence may be selected to optimize expression in a particular host organism by utilizing known preferred codons for the host organism of choice.

In another preferred embodiment, the isolated nucleic acid comprises the sequence set forth in SEQ ID NO. 13. In another preferred embodiment, the isolated nucleic acid comprises the sequence of nucleotides 144 through 1484 of SEQ ID No. 13. Fragments of a nucleic acid having the sequence of SEQ ID No. 13 that maintain the ability to encode a functional lepidopiteran glutamate-gated chloride channel are also encompassed by the present invention.

The present invention further encompasses nucleic acids isolatable from lepidoptera and capable of hybridizing under high stringency conditions to the complement of a nucleic acid having the sequence of nucleotides 144 through 1484 of SEQ ID NO: 13. Nucleic acid hybridization conditions are known to those of ordinary skill in the art and disclosed for example by Sambrook et al. (1989) Molecular Cloning—A laboratory manual, Cold Spring Harbor Laboratory Press. High stringency conditions are defined herein as 0.1× standard saline citrate (SSC), 0.1% sodium dodecyl sulfate (SDS) at 60° C.

In another embodiment, the present invention provides isolated nucleic acids having at least about 80%, and preferably at least about 90%, and more preferably at least about 95% sequence identify to the nucleic acid having the sequence of nucleotides 144 through 1484 of SEQ ID NO: 13. Sequence identity is determined using the program Clustal W described by Higgins et al. (1994) Nucleic Acids Res. 22:4673 and may be calculated using the EMBL Nucleotide Sequence Database (http://www.ebi.ac.uk/embl.html). The ability of the isolated nucleic acid of the present invention to encode a functional glutamate-gated chloride channel can be determined by functional assays as described hereinbelow.

A protein having the amino acid sequence of SEQ ID NO: 14 has glutamate-gated chloride channel activity. Analysis of the amino acid sequence and alignment with the sequence of the Drosophila glutamate-gated chloride channel indicates that the sequence of SEQ ID NO: 14 contains four membrane spanning regions at amino acids 246–268, 274–293, 309–328 and 415–435. The amino terminal 20–30 amino acids encode a signal peptide. Amino acid changes may be tolerated in the signal peptide domain so long as the ability of the protein to insert into a selected cell membrane is maintained. Those of ordinary skill in the art can determine suitable modifications of the sequence of the signal peptide and can likewise determine the nucleic acid sequence encoding the modified signal peptide domain.

The nucleic acids of the present invention may be obtained by using a nucleic acid having the sequence of SEQ ID NO: 13 or a fragment thereof to probe a lepidopteran cDNA library. Such libraries may be made by well-known methods, described for example in Sambrook et al., supra, or may be obtained commercially. The identity of the nucleic acid may be confirmed by nucleotide sequencing or by expression and functional analysis as described hereinbelow.

The present invention is further directed to vectors comprising the isolated nucleic acids of the present invention. In the vectors of the present invention, the nucleic acid encoding a lepidopteran glutamate-gated chloride channel is operably linked to suitable transcriptional and/or translational regulatory elements to effect expression of the glutamate-gated chloride channel in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and vectors into which the nucleic acid of the invention can be inserted are also commercially available. Recombinant viral vectors, including retrovirus, baculovirus, parvovirus and densovirus vectors are particularly preferred.

In a preferred embodiment the vector comprises a strong constitutive or inducible promoter operably linked to a nucleic acid encoding a lepidopteran glutamate-gated chloride channel. Suitable promoters are well known and readily available to one of ordinary skill in the art, and include for example, the polyhedrin promoter (Kitts et al., 1993, Bio Techniques, 14:810), heat shock promoter (Stellar et al., 1985, EMBO J., 4:167) and metallothionein promoter (Kaufman et al., 1989, Cell 59:359). Expression vectors can be constructed by well known molecular biologial methods as described, for example, in Sambrook et al. (1989) Molecular Cloning: A Laboratory Manual, Cold Spring Harbor Laboratory Press, Cold Spring Harbor, N.Y., or any of a myriad of laboratory manuals on recombinant DNA technology that are widely available. Expression vectors into which the nucleic acids of the present invention can be cloned under the control of a suitable promoter are also commercially available.

Another embodiment of the present invention provides host cells containing the vectors described above. The host cell may be procaryotic or eukaryotic, including bacterial, yeast, insect or mammalian. Insect and mammalian cells are preferred. Particularly preferred host cells include insect cell lines, including for example *Spodoptera frugiperda* cells. The host cells may be transformed, transfected or infected with the expression vectors of the present invention by methods well-known to one of ordinary skill in the art. Transfection may be accomplished by known methods, such as liposome mediated transfection, calcium phosphate mediated transfection, microinjection and electroporation. Permanently transformed insect cell lines are particularly preferred. For example, insect cell lines such as Drosophilia cell line SH1 can be transformed with the expression vectors of the present invention by commercially available lipofectin (GIBCO-BRL) to provide permanently transformed cell lines expressing a functional glutamate-gated chloride channel. In a preferred embodiment, the vector is designed such that expression of the protein is inducible.

Expression systems utilizing baculovirus vectors and insect host cells are preferred. The use of baculoviruses as recombinant expression vectors to infect lepidopteran insect cells is known in the art and described for example by Luckow et al. (1988) Bio/Technology 6:47–55 and Miller (1988) Ann Rev Microbiol. 42:177–199. The baculovirus vectors generally contain a strong baculovirus promoter operably linked to a nucleic acid of the present invention such that the promoter directs expression of the lepidopteran glutamate-gated chloride channel. Baculovirus polyhedrin promoters such as the Autographa califomica nuclear polyhydrosis virus polyhedrin promoter are preferred.

The baculovirus expression vectors of the present invention are made by inserting the nucleic acid encoding the lepidopteran glutamate-gated chloride channel downstream of the polyhedrin promoter in a baculovirus transfer vector, for example pBacPac8 available from Clontech or Bac-to-Bac available from Life Technologies. Baculovirus transfer vectors further contain flanking baculovirus sequences that allow homologous recombination between the transfer vector and baculovirus DNA during co-transfection. The transfer vector containing the nucleic acid of the invention and viral DNA are used to co-transfect insect cells. In a preferred embodiment the insect cells are Spodoptera. *Spodoptera frugiperda* cells including *Sf*9 are particularly contemplated. During co-transfection, homologous recombination results in the transfer of an expression cassette containing the polyhedrin promoter and the nucleic acid of the present invention to the polyhedrin locus of the viral DNA. The resulting recombinant virus is used to generate viral stocks by standard methods. Insect host cells are infected with the recombinant virus to produce insect cells expressing the glutamate-gated chloride channel.

The present invention is further directed to recombinant glutamate-gated chloride channel. The recombinant lepidopterant glutamate gated chloride channel may be isolated in a membrane preparation or present in the cell membrane of the host cell in which it has been recombinantly produced. Whole cells and membrane preparations comprising the recombinant lepidopteran glutamate-gated chloride channel are particularly contemplated. Recombinant lepidopteran glutamate-gated chloride channel is useful, for example, to screen potential insecticides by specific binding assays or functional assays.

The present invention further provides a method of making a recombinant lepidopteran glutamate-gated chloride channel. Recombinant lepidopteran glutamate-gated chloride channel is made by transforming, transfecting or infecting a suitable host cell with an expression vector comprising a nucleic acid encoding a lepidopteran glutamate-gated chloride channel, culturing the host cell under conditions suitable for expression, and optionally recovering the recombinant lepidopteran glutamate-gated chloride channel. A suitable host cell is any cell in which the nucleic acid encoding the transporter can be expressed to provide a functional glutamate-gated chloride channel. In a preferred embodiment, the recombinant lepidopteran glutamate-gated chloride channel is made in insect cells, preferably *Spodoptera frugiperda* 9 (*Sf*9), by infecting the insect cells with a recombinant virus in which the nucleic acid of the invention is under the control of a promoter suitable for use in *Sf*9 cells, such as a polyhedrin or TE1 promoter, and culturing the cells under conditions suitable for expression of the recombinant lepidopteran glutamate-gated chloride channel. In another preferred embodiment, the recombinant lepidopteran glutamate-gated chloride channel is made in permanently transformed cell lines as described above.

A functional lepidopteran glutamate-gated chloride channel can be identified by one of ordinary skill in the art by functional assays. An exhaustive review of techniques and protocols is provided in Rudy et al., eds. (1992) Methods in Enzymology 207, Academic Press, Inc., San Diego, Calif. For example, two-electrode voltage clamp recordings of host cells or oocytes expressing the lepidopteran glutamate-gated chloride channel can be used to assess chloride flux in response to application of glutamate or ivermnectin phosphate. Dose-dependent glutamate-evoked currents indicate the presence of a functional glutamate-gated chloride channel. Also, the activation of a membrane current by about 100 $\mu$m glutamate or 1 $\mu$m ivermectin phosphate is indicative of a functional glutamate-gated chloride channel.

The present invention further provides an amphibian oocyte comprising a nucleic acid encoding a functional glutamate-gated chloride channel, and an amphibian oocyte expressing a functional glutamate-gated chloride channel. The oocytes are useful as a system for screening potential insecticides useful against insects of the order lepidoptera. Such oocytes can be made using the nucleic acids of the invention and methods known in the art. In a preferred embodiment, the oocyte is *Xenopus laevis* oocyte. For example, expression vectors containing cDNA encoding the glutamate-gated chloride channel under the control of a strong promoter can be injected into the nuclei of oocytes, after which oocytes are incubated for from one to several days, followed by assessment for the presence of functional glutamate-gated chloride channel. Alternatively, mRNA can be synthesized in vitro from cDNA encoding the glutamate-gated chloride channel, and injected into oocytes, followed by assessment for the presence of functional glutamate-gated chloride channels as described hereinabove.

The present invention further provides methods of identifying agents that modulate the activity of a lepidopteran glutamate-gated chloride channel, and also encompasses novel agents identified by such methods. The agent may be an agonist, i.e. it mimics the action of glutamate by activating chloride flux, or an antagonist, i.e. it decreases the glutamate-activated chloride flux. The agent may be nucleic acid, peptide, protein, a non-protein organic molecule, or any other molecule capable of modulating the activity of the glutamate-gated chloride channel.

A method of identifying an agonist comprises applying the putative agonist to a Xenopus oocyte, a cell or membrane expressing the lepidopteran glutamate-gated chloride in the presence of chloride ions, and measuring chloride flux, wherein flux of chloride is indicative of an agonist. A method of identifying an antagonist comprises applying glutamate to Xenopus oocyte or a cell or membrane expressing the lepidopteran glutamate-gated chloride channel in the presence of chloride ions and measuring chloride flux; applying the putative antagonist and then, for example after about one minute, applying glutamate to the cell or membrane and measuring chloride flux; and comparing the chloride flux obtained in the presence of glutamate alone to the flux obtained under similar conditions in the presence of both putative antagonist and glutamate, wherein a decrease in flux of chloride observed in the presence of the putative antagonist relative to the flux observed in the presence of glutamate alone is indicative of an antagonist. In a preferred embodiment, chloride flux is measured by voltage clamp electrophysiology. In another preferred embodiment, the cell is an recombinant baculovirus-infected *Sf*9 cell or a permanently transformed cell line. In another preferred embodiment, the concentrations of agonists, antagonists and GABA are from about 0.1 nM to about 1.0 mM.

Agonists and antagonists against the lepidopteran glutamate-gated chloride channel can also be identified by ligand binding assays. Agonists and antagonists are identified by their ability to displace radiolabeled ligands known to act as agonists or antagonists, respectively. The recombinant glutamate-gated chloride channel, present in an oocyte, cell, or membrane, (preferably a membrane) is incubated with radiolabeled ligand and unlabeled candidate agonist or antagonist. After incubation, the incubation mixture is filtered, and radioactivity retained on the filters is measured by methods known in the art, for example liquid scintillation counting. The ability of the candidate compound to inhibit specific binding of the radiolabeled ligand provides a measure of the compound's agonist or antagonist activity. Suitable ligands include glutamate and ivermectin phosphate.

Agents identified by the foregoing methods may be useful as insecticides. Agents identified by the present methods may be assessed for insecticidal activity by in vitro and in vivo methods known in the art.

Another embodiment of the present invention provides a composition comprising a recombinant lepidopteran glutamate-gated chloride channel in a cell membrane. The composition may be a membrane preparation, including a freeze dried membrane preparation, or an intact cell or oocyte expressing the functional lepidopteran glutamate-gated chloride channel. The composition is useful, for example, to screen for potential insecticides by functional or specific binding assays. The composition may further comprise appropriate carriers or diluents, including, for example, physiological bufers.

The present invention further provides a kit for identifying agents that modulate the activity of a lepidopteran glutamate-gated chloride channel. The kit contains a first container containing a recombinant lepidopteran glutamate-gated chloride channel in a cell membrane. The membrane may be in the form of a membrane preparation, including a freeze dried membrane preparation, or an insect cell or oocyte expressing the functional lepidopteran glutamate-gated chloride channel. The kit of the present invention optionally further comprises glutamate. The compositions and kits of the present invention are useful for identifying insecticides.

All references cited herein are incorporated in their entirety.

The following nonlimiting examples serve to further illustrate the present invention.

EXAMPLE 1

RNA Isolation

*Heliothis virescens* embryo were isolated from eggs just before hatching obtained from Rhone-Poulenc in-house insectary, and *Heliothis virescens* muscles were obtained by dissecting early 5$^{th}$ instar *Heliothis virencens* larva to remove the fat body, gut, and central nervous system. Eggs and remaining larva skins were frozen in liquid nitrogen, and ground to powder. Powders were added to lysis buffer, and homogenized before proceeding with manufacturer's instruction for total RNA isolation using Poly(A) Pure™kit from Ambion. Poly A$^+$ RNA were selected twice by going through a oligo dT column. The RNA recovered from the column was dissolved in diethylpyrocarbonate (DEPC)-treated water. RNA was quantified by spectrophotometry and separated on a denaturing agarose gel to check its integrity before use in RT-PCR and cDNA library construction.

PCR Using Degenerate Primers

Two degenerate oligonucleotides, mw 01 and mw 02, were designed and synthesized from highly conserved regions found in glutamate-gated chloride channel family following the amino acid sequence for *Drosophila melanogaster* GluCl (Cully et al. (1996) J. Biol. Chem. 271:20187), *Caenorhabditis elegans* GluCl-α and *C.elegans* GluCl-β (Cully et al. (1994) Nature 20:371). Primer mw01 has the sequence 5'-GGATGCC(ATGC)GA(TC)(TC)T(ATGC)TT(TC)TT-3'. (SEQ ID NO.: 1) Primer mw02 has the sequence 5'-TC(ATGC)A(AG)CCA(AG) AA(ATGC)(GC)(AT)(ATGC)ACCC-3'. (SEQ ID NO:2). The primer mw01 was located upstream of the transmembrane (TM) domain 1, while downstream primer mw 02 was located within the TM domain 1. The primer mw 02 was used to synthesize first strand cDNA from mRNA isolated from Heliothis embryo using Boehringer Mannheim's 1$^{st}$ Strand cDNA Synthesis Kit for RT-PCR. The cDNA was used as the template for a hot start PCR mix (100 µl) containing: 0.8 mM dNTP's, 2 mM MgCl$_2$, 1.2 pmol/µl degenerate primers and 5 U Pfu DNA polymerase (Stratagene). The a amplification was performed using 35 cycles of denaturation at 94° C. for 1 min, annealing at 53° C. for 1 min and elongation at 72° C. for 1 min. The denaturation step of the first cycle was 5 min long and the elongation step of the last cycle was 10 min (Perkin Elmer, DNA Thermal Cycler 480) (Sambrook et al., 1989, Molecular Cloning—A laboratory Manual. Cold Spring Harbor Laboratory. Press).

PCR generated a 451 base pair (bp) fragment which was cloned into the pCR-Blunt vector (Invitrogen) to produce pE6 and sequenced. The amplified fragment had the following sequence:

```
5'-GGA TGC CGG ATT TGT TTT TCT CCA ACG AGA AGG AAG GTC ATT TCC ACA AC

A TCA TCA TGC CGA ACG TGT ACA TCC GGA TCT TCC CCA ACG GCA ACG TGC TGT

ACA GCA TCC GAA TCT CCT TGA CGC TCT CGT GCC CCA TGA ACC TCA AGT TGT

ACC CCC TGG ATA AGC AGA CCT GCT CGC TGA GGA TGG CTA GTT ATG GTT GGA

CCA CAG ACG ACT TAG TGT TCC TAT GGA AGG AAG GCG ACC CGG TGC AGG TGG

TGA AGA ACT TAC ACC TGC CTC GGT TCA CGA TGG AGA AGT TCC TCA CTG ACT

ACT GCA ACA GTA AGA CTA ATA CCG GTG AAT ACA GTT GCC TGA AGG TAG ACT

TGC TCT TCA AAC GCG AGT TCA GTT ACT ACC TGA TCC AGA TCT ACA TTC CGT GCT

GCA TGC TGG TCA TCG TGT CCT GGG TCA CCT TTT GGC TCG A-3'(SEQ ID NO:3).
```

Rapid Amplification of cDNA Ends (RACE-PCR)

RACE reactions (Frohman et al. 1988 Proc. Natl. Acad. Sci. USA 85:8998), used to obtain the 5' and 3' ends of the *Heliothis virescens* mRNA, was performed using synthesized double stranded cDNA as the template. Two microgram of polyA mRNA from either *Heliothis virescens* embryo or muscle were used to synthesize cDNA with a Marathon cDNA amplification kit (CLONTECH) following the manufacturer's instructions. Specific primer mw03, derived from 451 bp fragment and having the sequence 5'-CCTGCACCGGGTCGCCTTCCTTCC-3',(SEQ ID NO:4) along with the adaptor primer (AP1, 5'-CCATCCTAATACGACTCACTATAGGGC-3')(SEQ ID NO: 5) provided in the kit were used for the amplification of 5' cDNA end. Primer mw04, derived from 451 bp fragment and having the sequence 5'-TACAGCATCCGAAT CTCCTTGACGC,(SEQ ID NO: 6)along with the primer AP1 were used for the amplification of 3' cDNA end. The PCR reactions were carried under the same conditions as in above section except using "touchdown PCR", which was performed using 5 cycles of denaturation at 94° C. for 30 sec, annealing and elongation at 72° C. for 4 min; 5 cycles of denaturation at 94° C. for 30 sec, annealing and elongation at 70° C. for 4 min; and 25 cycles of denaturation at 94° C. for 20 sec, annealing and elongation at 68° C. for 4 min. The denaturation step of the first cycle was 1 min at 94° C. One tenth of the PCR reaction (10 µl) was separated on a 1.2% agarose gel containing 1 µl/ml ethidium bromide. The amplified fragments from both 5'RACE and 3'RACE were cloned into pCR2.1 vector (Invitrogen) to produce plasmids designated p5'E4 and p3'M5, respectively. Fragment in p5'E4 has the following sequence:

CGC TGA GCA TTG CGA ACT ACG CCT TCA ACA TTG TTT TTT TAA ACA AGC ACC
GTT TTT TAA TTT TAA AAG CTC TCA TTA AAG GTT TTA TTT GAA GGA AAG TTG TGA
CAG CAA CCG GAG TCG TTT AGA ATG GGA CTT TGT TGA GTC AGA GGA TGG ACA
TCC CGC GGC CAT CAT GCG CCC TCG TAT GGT GTT GTT TAT TTG TCA CCC ATC TCT
CAG AAT GCA TGA ACG GTG GGA AGA TCA ACT TCC GAG AGA AGG AGA AGC AGA
TCC TGG ATC AGA TCC TGG GCC CCG GGA GGT ACG ACG CCA GGA TCA GAC CCT
CGG GGA TCA ACG GCA CCG ATC GGC CAG CGG TAG TGA GCG TCA ATA TAT TTG
TCC GAA CTA TAT CAA AGA TCG ATG ATG TCA CAA TGG AAT ACT CCG TAC AGT
TAA CGT TTC GGG AAC AAT GGT TAG ATG AAC GGC TCA AAT TCA ATA ATC TTG
GAG GTC GCC TCA AAT ACC TGA CGC TTA CCG AAG CCA ACA GAG TCT GGA TGC
CTG ATC TAT TCT TCT CCA ACG AGA AGG AAG GTC ATT TCC ACA ACA TCA TCA
TGC CGA ACG TGT ACA TCC GAA TCT TCC CCA ACG GCA ACG TGC TGT ACA GCA
TCC GAA TCT CCC TGA CGC TCT CGT GCC CCA TGA ACC TCA AGT TGT ACC CCC
TGG ATA AGC AGA CCT GCT CGC TCA GGA TGG CTA GTT ATG GTT GGA CCA CAG
ACG ACT TAG TGT TCC TAT GGA AGG AAG GCG ACC CGG TGC AGG (SEQ ID NO:7).

Fragment in p3'M5 has the following sequence:

5'-CGC TCT CGT GCC CCA TGA ACC
TCA AGT TGT ACC CCC TGG ATA AGC AGA CCT GCT CGC TCA GGA TGG CTA GTT
ATG GTT GGA CCA CAG ACG ACT TAG TGT TCC TAT GGA AGG AAG GCG ACC CGG
TGC AGG TGG TGA AAA ACT TAC ACC TGC CTC GGT TCA CGC TGG AGA AGT TCC
TCA CTG ACT ACT GCA ACA GTA AGA CTA ATA CCG GTG AAT ACA GTT GCC TGA
AGG TAG ACC TGC TCT TCA AAC GCG AGC TCA GTT ACT ACC TGA TCC AGA TCT
ACA TTC CGT GCT GCA TGC TGG TCA TCG TGT CCT GGG TGT CCT TCT CCT GGC TGG ACC
AGG GAG CTG TGC CTG CGA GGG TCT CAC TAG GAG TGA CGA CTT TAC TTA CAA
TGG CGA CCC AGT CGT CAG GCA TCA ACG CGT CCC TAC CAC CGG TGT CCT ACA
CGA AAG CCA TTG ATG TCT GGA CTG GTG TAT GTC TCA CAT TCG TAT TCG GAG
CGC TAC TAG AGT TCG CGC TCG TCA ACT ATG CGT CTC GCT CTG ACA TGC ACC
GAG AGA ACA TGA AGA AAG CGA GAC GGG AGA TGG AAG CAG CCA GCA TGG ATG
CTG CCT CAG ATC TCC TTG ATA CAG ATA GCA ACA CC A CC TTT GCT ATG AAA CCC
TTG GTG CGC GGC GGC GTG GTG GAA TCC AAG ATG CGG CAG TGC GAG ATC CAC
ATC ACC CCG CCG CGG AAG AAC TGC TGC CGC CTG TGG ATG TCC AAG TTC CCC
ACG CGC TCC AAG ATC GAC GTC ATC TCC AGG ATC ACC TTC CCA CTT GTG TTC
GCT CTG TTT AAC CTG GCT TAC <u>TGA</u> ATG AAG CAG AGA AAC TCC TCC TTT GCG
CAC AGA AAT CCT GAA GAG ACT GAA CAA CGA AGT TTC CTA ACC ACA ATC ATT
GCT ATG ATT ATA CCG AGA ATT TAT TTT ATA CTA ATT GTT GTG ACC ACA CGG TTT
TAA CGT AGC TTG GAT CCA CGC GGT GTT AAT ATT TGT TGA TCG CTT AGA ATA
AAT AAA TAT GCT TTG TTG AAA AAA AAA AAA AAA AAA AAA AAA AAA AAA-3'(SEQ ID NO:8).

Generation of Full-Length cDNA by PCR

5' and 3'-end gene specific primers (GSP) were designed based on the sequence obtained from previous 5'- and 3'-RACE products. 5' GSP1 has the following sequences: 5'-GCTGAGCATTGCGAACTACGCCTTCAAC 3', (SEQ ID NO: 9) and 3' GSP2 has the following sequences: 5'-TAACACCGCGTGGATCCAAGCTACG 3'(SEQ ID NO: 10). Full-length cDNAs from both Heliothis embryo and muscle were generated using 5' GSP1 and 3' GSP2 in a long distance PCR reaction which used following cycle condition: 1 cycle of denaturation at 94° C. for 1 min, and 25 cycles of denaturation at 94° C. for 30 sec and annealing and extension at 72° C. for 5 min using pfu as polymerase. The amplified fragments from both Heliothis embryo and muscle were cloned into pCR2.1-TOPO vector (Invitrogen) to generate plasmids HEG3E(4)-2 and HEGM(1)-3. HEG3E(4)-2 has the following sequences (SEQ ID NO: 11):

```
   1  CTGAGCATTG CGAACTACGC CTTCAACATT GTTTCTTTAA ACAAACACCG TTTTTTAATT
  61  TTAATAGCAC TCATTAAAGG TTTTATTTGA AGGAAAGTTG TCACAGCAAC CGGAGTCGTT
 121  TAGAATGGGA CTTTGTTGAG TCGGAGGATG GACATCCCGC GGCCATCATG CGCCCTCGTA
 181  TTGGTGTTGT TATTTGTCAC CCATCTCTCA GAATGCATGA ACGGTGGGAA GATCAACTTT
 241  CGAGAGAAGG AGAAGCAGAT CCTGGATCAG ATCCTGGGCC CCGGGAGGTA CGACGCCAGG
 301  ATCAGACCCT CGGGGATCAA CGGCACTGAT GGGCCAGGGG TAGTGAGCGT CAATATATTT
 361  GTCCGAACTA TATCAAAGAT CGATGACGTC ACAATGGAAT ACTCCGTACA ATTAACGTTT
 421  CGGGAACAAT GGTTAGATGA ACGGCTCAAA TTCAATAATC TTGGAGGTCG CCTCAAATAC
 481  CTGACACTGA CTGAAGCCAA CAGAGTCTGG ATGCCTGATC TATTCTTCTC CAACGAGAAG
 541  GAAGGTCATT TCCACAACAT CATCATGCCG AACGTGTACA TCCGAATCTT CCCCAACGGC
 601  AACGTGCTGT ACAGCATCCG AATCTCCCTG ACGCTCTCGT GCCCCATGAA CCTCAAGTTG
 661  TACCCCCTGG ATAAGCAGAC CTGCTCGCTC AGGATGGCTA GTTATGGTTG GACCACAGAC
 721  GACTTACTGT TCCTATGGAA GGAAGGCGAC CCGGTGCAGG TGGTGAAAAA CTTACACCTG
 781  CCTCGGTTCA CGCTGGAGAA GTTCCTCACT GACTACTGCA ACAGTAAGAC TAATACCGGT
 841  GAATACAGTT GCCTGAAGGT AGACCTGCTC TTCAAACGCG AGTTCAGTTA CTACCTGATC
 901  CAGATCTACA TTCCGTGCTG CATGCTGGTC ATCGTGTCCT GGGTGTCCTT CTGGCTGGAC
 961  CAGGGAGCTG TGCCTGCGAG GGTCTCACTA GGAGTGACGA CTTTACTTAC AATGGCGACC
1021  CAGTCGTCAG GCATCAACGC GTCCCTAGGA CCGGTGTCCT ACACGAAAGC CATTGATGTC
1081  TGGACTGGGT TATGTCTCAC ATTCGTATTC GGAGCGCTAC TAGAGTTTGC GCTGCTCAAC
1141  TATGCGTCTC GCTCTGACAT GCACCGAGAG AACATGAAGA AAGCGAGACG GGAGATGGAA
1201  GCAGCCAGCA TGGATGCTGC CTCAGATCTC CTTGATACAG ATAGCAACAC CACCTTTGCT
1261  ATGAAACCCT TGGTGCGCGG CGGCGTGGTG GAATCCAAGA TGCGGCAGTG CGAGATCCAC
1321  ATCACCCCGC CGCGGAAGAA CTGTGGATGT CCAAGTTCCC CCAAGTTCCC CACGCGCTCC
1381  AAGAGGATAG ACGTCATCTC CAGGATCACC TTCCCACTTG TGTTCGCTCT GTTTAACCTG
1441  GCTTACTGAA TGAAGCAGAG AAACTCCTCC TTTGCGCACA GAAATCCTGA AGAGACTGAA
1501  CAACGAAGTT TCCTAACCAC AATCATTGCT ATGATTATAC CGAGAATTTA TTTTATACTA
1561  ATTGTTGTGA CCACACGGTT TTAACGTAGC TTGGATCCAC GCGGTGTTA
```

HEGM(1)-3 has the following sequence (SEQ ID NO: 12):

```
   1  AGGTGCGGAC GTCTGCACTT GCGAATCGAA GTGATAGAAA ATAGTTCGAT GAATACGGGA
  61  GTTTGAGTGG AGTGATTTAT AATTCGGAGG ATGGACATCC CGCGGCCATC ATGCGCCCTC
 121  GTATTGGTGT TGTTATTTGT CACCCATCTC TCAGAATGCA TGAACGGTGG GAAGATCAAC
 181  TTTCGAGAGA AGGAGAAGCA GATCCTGGAT CAGATCCTGG GCCCCGGGAG GTACGACGCC
 241  AGGATCAGAC CCTCGGGGAT CAACGGCACT GGCTATGCGC CAACGTTAGT CCATGTCAAC
```

```
                         -continued
 301    ATGTATCTAC GGTCCATCAG CAAAATAGAT GATTACAAAA TGGAATACTC CGTACAATTA

361    ACGTTTCGGG AACAATGGTT AGATGAACGG CTCAAATTCA ATAATCTTGG AGGTCGCCTC

421    AAATACCTGA CACTGACTGA AGCCAACAGA GTCTGGATGC CTGATCTATT CTTCTCCAAC

481    GAGAAGGAAG GTCATTTCCA CAACATCATC ATGCCGAACG TGTACATCCG GATCTTCCCC

541    AACGGCAACG TGCTGTACAG CATCCGAATC TCCCTGACGC TCTCGTGCCC CATGAACCTC

601    AAGTTGTACC CCCTGGATAA GCAGACCTGC TCGCTCAGGA TGGCTAGTTA TGGTTGGACC

661    ACAGACGACT TAGTGTTCCT ATGGAAGGAA GGCGACCCGG TGCAGGTGGT GAAAAACTTA

721    CACCTGCCTC GGTTCACGCT GGAGAAGTTC CTCACTGACT ACTGCAACAG TAACACTAAT

781    ACCGGTGAAT ACAGTTGCCT GAAGGTAGAC CTGCTCTTCA AACGCGAGTT CAGTTACTAC

841    CTGATCCAGA TATACATTCC GTGCTGCATG CTGGTCATCG TGTCCTGGGT GTCCTTCTGG

901    CTGGACCAGG GAGCTGTGCC TGCGAGGGTC TCACTAGGAG TGACGACTTT ACTTACAATG

961    GCGACCCAGT CGTCAGGCAT CAACGCGTCC CTACCACCGG TGTCCTACAC GAAAGCCATT

1021    GATGTCTGGA CTGGGTTATG TCTCACATTC GTATTCGGAC CGCTACTAGA GTTTGCGCTC

1081    GTCAACTATG CGTCTCGCTC TGACATGCAC CGAGAGAACA TGAAGAAAGC GAGACGGGAG

1141    ATGGAAGCAG CCAGCATGGA TGCTGCCTCA GATCTCCTTG ATACAGATAG CAACACCACC

1201    TTTGCTATGA AACCCTTGGT GCGCGGCGGC GTGGTGGAAT CCAAGATGCG GCAGTGCGAG

1261    ATCCACATCA CCCCGCCGCG GAAGAACTGC TGCCGCCTGT GGATGTCCAA GTTCCCCACG

1321    CGCTCCAAGA GGATAGACGT CATCTCCAGG ATCACCTTCC CACTTGTGTT CGCTCTGTTT

1381    AACCTGGCTT ACTGTTGGGG GGGCAAGAGG GGGGCGGTGG CTGCTACCAT GTCTTGCAGG

1441    AGCGATGAGA CTATTAATGC TATTTATAAG CTGATACAGA ATGAAGCAGA GAAACTCCTC

1501    CTTTGCGCAC AGAAATCCTG AAGAGACTGA ACAACGAAGT TTCCTAACCA CAATCATTGC

1561    TATGATTATA CCGAGAATTT ATTTTATACT AATTGTTGTG ACCACACGGT TTTAAGCTAG

1621    CTTGGATCCA CGCGGTGTTA
```

EXAMPLE 2

Isolation of Full-length Clone by Screening of cDNA Library

Compared to the glutamate-gated chloride channel clones from Drosophila and *C. elegans*, clone HEG3(E)-2 has a stop codon within the M4 transmembrane domain, whereas clone HEGM(1)-3 has an unusual long 3' sequence after the M4 transmembrane domain. It is unclear whether these two clones resulted from different RNA splicing or due to the errors introduced by PCR polymerase during the RACE reaction. cDNA libraries of *Heliothis virescens* embryo and muscle were constructed using 7.5 μg of each of isolated polyA mRNA with Stratagene's cDNA Synthesis kit. The cDNAs were made according to the manufacturer's instructions and then cloned into the lambda ZAP expression cloning vector and packaged with Gigapack III Gold packaging system (Stratagene) following the manufacturer's instructions. Thus two non-amplified libraries of $5 \times 10^5$ recombinants were made and then amplified.

Clone HEG3(E)-2 insert was cut out from its vector by SacI enzyme, and was labeled with $^{32}P$ using Boehringer Mannheim's Random Primed DNA Labeling Kit (Ca # 1004760). Part of the amplified *Heliothis virescens* embryo library was plated out on 10 large 150-mm NZY agar plate at 50,000 pfu/plate. Phage particles were transferred to nitrocellulose membranes. Membranes were denatured in a 1.5 M NaCl and 0.5 M NaOH denaturation solution for 5 minutes, neutralized in a 1.5 M NaCl and 0.5 M Tris-Cl (pH 8.0) neutralization solution for 5 minutes and rinsed in a 0.2 Tris-Cl (pH 7.5) and 2×SSC buffer for 2 minute. DNA was crosslinked to the membranes using the Stratalinker UV crosslinker (CL-100 Ultraviolet Crosslinker, UVP). Prehybridization was performed in a 50 ml solutions containing: 25 ml of formamide, 12.5 ml of 20×SSC, 0.5 ml of 10% SDS and 5 ml of Derhardt solution at 42C for 3–4 hours. Labeled probes were added to the prehybridization solution at $1.84 \times 10^5$ dpm/ml 32P and hybridization was continued at 42° C. for 24 hours. Membranes were washed twice for 15 minutes in low stringency conditions (2×SSC/0.1%SDS, room temperature), twice for 15 minutes in high stringency conditions (0.2×SSC/0.1%SDS, 42C), and once for 15 minutes in higher stringency conditions (0.1×SSC/0.1%SDS, 42C). Ten positive clones were identified and plaques were purified, and secondary and tertiary screenings were performed using the same primer with positive clones to make sure that each positive plaque was very well separated. The phagemids containing the inserts were excised following the manufacturer's instruction (Stratagene). Two clones which have the same full-length sequences of glutamate-gated chloride channels, were designated HEGE2. The following DNA sequence (SEQ ID NO: 13) for clone HEGE2 was determined:

```
   1  ACCAGGCGAA CTACGCCTTC AACATTGTTT TTTTAAACAA ACACCGTTTT TTAATTTTAA
  61  TAGCTCTCAT TAAAGGTTTT ATTTGAAGGA AAGTTGTGAC AGCAACCGGA GTCGTTTAGA
 121  ATGGGACTTT GTTGAGTCGG AGGATGGACA TCCCGCGGCC ATCATGCGCC CTCGTATTGG
 181  TGTTGTTATT TGTCACCCAT CTCTCAGAAT GCATGAACGG TGGGAAGATC AACTTTCGAG
 241  AGAAGGAGAA GCAGATCCTG GATCAGATCC TGGGCCCCGG GAGGTACGAC GCCAGGATCA
 301  GACCCTCGGG GATCAACGGC ACTGATGGGC CAGCGGTAGT GAGCGTCAAT ATATTTGTCC
 361  GAAGTATATC AAAGATCGAT GACGTCACAA TGGAATACTC CGTACAGTTA ACGTTTCGGG
 421  AACAATGGTT AGATGAACGG CTCAAATTCA ATAATCTTGG AGGTCGCCTC AAATACCTGA
 481  CACTGACCGA AGCCAACAGA GTCTGGATGC CTGATCTATT CTTCTCCAAC GAGAAGGAAG
 541  GTCATTTCCA CAACATCATC ATGCCGAACG TGTACATCCG GATCTTCCCC AACGGCAACG
 601  TGCTGTACAG CATCCGAATC TCCTTGACGC TCTCGTGCCC CATGAACCTC AAGTTGTACC
 661  CCCTGGATAA GCAGACCTGC TCGCTCAGGA TGGCTAGTTA TGGTTGGACC ACAGACGACT
 721  TAGTGTTCCT ATGGAAGGAA GGCGACCCGG TGCAGGTGGT GAACAACTTA CACCTGCCTC
 781  GGTTCACGCT GGAGAACTTC CTCACTGACT ACTGCAACAG TAAGACTAAT ACCGGTGAAT
 841  ACAGTTGCCT GAAGGTAGAC TTGCTCTTCA AACGCGAGTT CAGTTACTAC CTGATCCAGA
 901  TCTACATTCC GTGCTGCATG CTGGTCATCG TGTCCTGGGT GTCCTTCTGG CTGGACCAGG
 961  GAGCTGTGCC TGCGAGGGTC TCACTAGGAG TGACGACTTT ACTTACAATG GCGACCCAGT
1021  CGTCAGGCAT CAACGCGTCC CTACCACCGG TGTCCTACAC GAAAGCCATT GACGTCTGGA
1081  CTGGTGTATG TCTCACATTC GTATTCGGAG CGCTACTAGA GTTCGCGCTC GTCAACTATG
1141  CGTCTCGCTC TGACATGCAC CGAGAGAACA TGAAGAAAGC GAGACGGGAG ATGGAAGCAG
1201  CCAGCATGGA TGCTGCCTCA GATCTCCTAG ACACAGATAG CAACACCACC TTTGCTATGA
1261  AACCCTTGGT GCGCGGCGGC GTGGTGGAAT CCAAGATGCG GCAGTGCGAG ATCCACATCA
1321  CCCCGCCGCG GAAGAACTGC TGCCGCCTGT CCATGTCCAA GTTCCCCACG CGCTCCAAGA
1381  GGATCGACGT CATCTCCAGG ATCACCTTCC CACTTGTGTT CGCTCTGTTT AACCTGGCTT
1441  ACTGGTCGAC GTACCTGTTC CGCGACGAGG ACGAGGAGAA GTGATTCTCC GAGTCCCTGG
1501  AGAGGGGCGT GGGGCCGCGC GTGCAGCTGG TGGCGGCCGT CGTGATGCCC TACGTGCTGT
1561  TCGTGGTGGC GTACTCGCTG TGCTTCCGCG CGCGCGCCCC GCCCCCTTCG CCCCCGCCCG
1621  CGCCCGCGCC CGCGCCCGCG CCCGCACCCT CCCGCCGCAG CGCGCGCGCA CGCACACAAG
1681  CACACCCACC TAGCCCGCTC TAGCGAACTC ACCCCATTCA TTATCGTGAC ATATTATATT
1741  ATCGTGTATT TTAATCGACG TCTTCCTCGT GGCAGCGTTA TTCCCACTCA GTATTCGATG
1801  GCGTTAGTGT AATTAGTAAA GCTCAAGTGT CTATTTGTAT ATATATGTGA CCCCCGTGCC
1861  AGTTTAGACC AAGCCTCCGT TTTTAAATTG AAGCAGTTCG AGAAAAACGG TAAAAATAGA
1921  CTCAATTTTG ATTGGTCATC TAAACAGCAG AACTTTTATT CGGCACTTAT AAAGTCCTCA
```

-continued

```
1981  ATTATTTGTG TACAAAAATA AATATTTTAC TTTCCGAGAA TTAAAAATTT TCGATAATTT

2041  TACCAATGAT ATGACTCCTT GTATGGATTC GTATGTAATG TAAACCTAGG TTAAGATATA

2101  AGAGGAATCC CAGAGGTTCC CGCATATTAC TTTAGCCTTT AAAGTAAGGT AAATAAGGAC

2161  TAGAATGGCA CTAATGTGTA GTGGAAGTGG GGTATTATTT AGTAGTTTTC ACTCTACAGT

2221  ACGTGAACTG GACTAGATCT ACTAGCAAAT AGAGTTGATC AATTTTCATG TCGAAATGTT

2281  CACAGATATT GTATAAACCG CTGGAGGTAA ACAGCTATCA ACAATGTAAC ACCAAATACC

2341  ATCAGAATCA AGCAAAACCA TGGAAATTTT GCTAATCGAA AAGTTGTAAC TGTTTATCTA

2401  TGGCAGGTAT AATTGGCCTA GTAATGTATC GTGTAGTATC ATTTACAACA CATATTAACT

2461  ATTAACCACA TTATGTGAAA GAAGGAATTT ATAAAAAAAA CCTTATTAAA TATATATTAG

2521  ATAAGTATTA TTAATTGGAT ATTCTCTTGC TGGGGATTTT AATATGAATC TTACCTTTAA

2581  ATAAGTTTGA TCTCACTAGA CGTTGCAAAT GGATACCCCA ATACCTTTT CCGCATTAAA

2641  AGGTATTATT TTAACAAATG TATTCTTCCC CGTCAATGTT TTAAGACTAC GTATCTACAT

2701  AAAATGATGT ATTGTTCATA CAATACTATT TCAAAATGCA AGAACAACGT AAAGTGCATT

2761  TCATTGATGT TTGTGTATGT AGATGACATT AGTATTTTAC CCAAAAATAC TGATATTAAA

2821  ATTCCCAGTA AGATTCGTAG GTAAATGGTA AACGTGTAAA TAGTTGGGCC TACAACTTTC

2881  TACACCTGTG TCGCTCAGTG TACAGTTACC TATATTTAAT ATTACAATTA TATCATTATT

2941  AACGAATGAT AAGATTTTAT TAACATTAAT TTCTCTGTCT GAACGTATCA CTGTAAATAT

3001  TACTAAATGT TTCCTAATTA CATTATTCAT ACATATATTA TCATCCCTTG AGCTATAGTT

3061  GCAAAGTATT CCAAAACCAC AATGAAAATA AAATTTCAAT TTACTTCACG ATCACCAAAT

3121  TGTGAAAACC TGGTTGTTCT GAATTCATTT AACAATTAGT TTTTACTTTG AATCCATGGC

3181  TCAAGGGACA TCCTAAGGAT ATTCATTGAA ATCTATTTAG AATCTCGTGT ATGTATCATG

3241  ACACCTTCAA ATAAAATATC ACTAATGCTG TGTTCGGCTA TTAGATACAA TAAGTCGTAC

3301  ATATTAACGT AAGCACATTC GTTTTTATTA TGCGGCGGAG AGAACGCATC TGTTTCTATA

3361  ACGAAAGGGT GGCCATTATC GGCTATATCA TCTTGCTTGG TCTGTATAAA AATAAGAGTC

3421  AAAGACTCGG GGGAAACCCC TATATGTATA CTATCATAAC CGTTATCCTT ATTTTGACAA

3481  AGCTCTGGGA AACGAAATAG CATTTTGTTT CAATTACACA ATTCTTGCTC ATTTTTCTCT

3541  TCCGCCTTTT ATTTCAATTT AGGTGTTGCC CACTGTGCGC AATACTCTAA TGGCTTAGAA

3601  TTATCCTTAA TATATATTCT CGGGCTGTGA CGAGGTGTAG CATCTGCATT ATTATATTAA

3661  TGTCATTTCG TTTGCCATTC GTTGTATGTA AGGAAATATT AGCCTATGTC CAACGCTCAA

3721  AATCTCATAG ACGTATTAGG CACACATAAG TGTACCTTTT CGTATGTATG TAAATTATTG

3781  GAGACTCAAT GTCTTAGTTG GTGCTATATA TACTACGATC CGAGGAGAAT GTACCCAGTA

3841  GTTTACTCAT ACATAACGCC ACTGATATCT TGTGGAGGAA ATATTATCTG CGAGACAAGT

3901  AGACATTAGT TAAGTTTACA TATTTACAAT AAATGTTTCC ATTATTAGGA TATAACATAT

3961  GAATGTGTTA CTGTTGAAAG CAGCTTCTCA AGGTACCACC AGTAATTCGG AGATACTTGT

4021  AGGATTTGCA TTCGATAAAC AACTTATACT AAAACGAAGA TTTGACTGAA TCTAAACCGC
```

-continued

```
4081   AAATACTGTG GTCAAAATTA TTAAACACTT TCAATACATG TTGTACGCAT GTTTCTGTAA
4141   TTTCACATTT AATTGTAAAG TCAATTAAAT CACTGTATAA TAATACATTT TCAACATATC
4201   TCTCACTGTT AAGATTTCGG TTGGTCCAAC GACAGAATCA AATCGCAACG TAATGATGAT
4261   CCGGGCAAAA CTAACAACTA GATAGATCTC TTAAATGATT ACGTTGAAGT GGAAGAGGTG
4321   ATGTATGAAG GAAGGTAGGA TTAAGTAACA CTGTATAATA TATTGACCAT AATTACGATT
4381   TTAGAAGTCA TAATGGACGG TTTACCTCTT AAGATTATAC AGTAAAGGTA GATAGTTTCA
4441   TTCGTAAGCT ATGTTGTACT CGATTGGTAT GACATAACTA ATGACTGAGC TTTGTCATCT
4501   ACTACAACCC GAGGGCGAAT ACCTCCTTCT TCTACCATTC CCATTTAATT ATAAAGAAAC
4561   ATTGTAAAAA ATGATTTAAT AAAATATCCC AAATATCTTA AAACAAAAAA AAAAAAAAAA
4621   A
```

Sequencing indicated that HEGE2 encoded a full length *Heliothis virescens* glutamate-gated chloride channel clone directionally cloned into the EcoRI and XhoI sites of phagemid pBluescript SK (+/−). The coding sequence starts at 144 bp and ends at 1484 bp, and encodes a polypeptide of 444 amino acids having the predicted sequence (SEQ ID NO: 14):

```
MDIPRPSCALVLLFVTHLSECMNGGKINFREKEKQILDQILGPGRYDARIRPSGINGTDGP
AVVSVNIFVRSISKIDDVTMEYSVQLTFREQWLDERLKFNNLGGRLKYLTLTEANRVW
MPDLFFSNEKEGHFHNIIMPNVYIRIFPNGNVLYSIRISLTLSCPMNLKLYPLDKQTCSLR
MASYGWTTDDLVFLWKEGDPVQVVKNLHLPRFTLEKFLTDYCNSKTNTGEYSCLKVD
LLFKREFSYYLIQIYIPCCMLVIVSWVSFWLDQGAVPARVLLGVTTLLTMATQSSGINAS
LPPVSYTKAIDVWTGVCLTFVFGALLESRFVNYASRSDMHRENMKKARREMEAASMD
AASDLLDTDSNTTFAMKPLVRGGVVESKMRQCEIHITPPRKNCCLWMSKFPTRSKRID
VISRITFPLVFALFNLAYWSTYLFRDEDEEK
```

BLAST Search

BLAST search (http://www.ncbi.nlm.gov) and amino acid sequence comparison were used to identify glutamate-gated chloride channel-like fragments from the PCR products amplified with degenerate primers, the PCR products obtained from RACE and clones screened from embryo cDNA library. BLAST was also used to determine the orientation and the position of the amplified products compared to the entire cDNA sequence.

EXAMPLE 3

Expression of Nucleic Acid Encoding Lepidopteran Glutamate-gated Chloride Channel in Xenopus Oocytes:

Messenger RNA was produced from the cDNA template of HEGE2 by in vitro transcription with the Ambion mMESSAGE mMACHINE IN VITRO TRANSCRIPTION KIT (Ambion, Inc.). The mRNA was injected into oocytes by the following procedure.

Frogs were anesthetized in a 2 gram/liter solution of 3-amino benzoic acid ethyl ester for thirty minutes, after which oocytes were surgically removed from the abdominal cavity. Follicles were digested by collagenase treatment under sterile conditions by standard methods. Oocytes were injected with 50 nl of 1 $\mu g/\mu l$ mRNA by glass electrodes.

After a 24 hr incubation, two-electrode voltage clamp recordings were made. Recordings were made using a Dagan, TEV200 voltage clamp interfaced with a MacLab4 data acquisition system running the MacLab Chart data acquisition/analysis software. Oocytes were positioned under a dissection scope under constant perfusion with frog saline (96 mM of NaCl, 2 mM of KCl, 1 mM of $MgCl_2$, 1.8 mM of $CaCl_2$ and 10 mM of HEPES, pH 7.5) using a Razel syringe perfusion pump. Model A99-FY at 93.9 cc/hr. Glass electrodes (A-M Systems. Inc. 1.5 mm×0.86 mm) were filled with 3 M KCl and resistance (a function of the diameter of the channel opening) was measured to be between 0.7 and 1.5 mega ohms. Both electrodes were inserted into the oocyte at opposite sides, the resting potential was recorded and the voltage clamp turned on. Oocytes were held at a resting potential at −80 mV. Control responses of glutamate were obtained by stopping the perfusion of saline and perfusing with a known concentration of glutamate in frog saline. The average of several glutamate applications was taken as the maximal chloride current for that particular glutamate dose. The effect of 100 micromolar glutamate on the lepidopteran glutamate-gated chloride channel expressed in Xenopus oocytes is depicted in FIG. 1. Glutamate application is indicated by the arrow marked "on". The data in FIG. 1 indicate that 100 uM glutamate activate a membrane current in Xenopus oocytes injected with 50 ng of HEGE2 mRNA. This example demonstrates that the expression of mRNA corresponding to the cDNA in HEGE2 results in a functional glutamate gated chloride channel in oocytes. One micromolar of Ivermectin phosphate also slowly and irreversibly activated current in oocytes.

We claim:

1. A method of identifying an agent that modulates the activity of a lepidopteran glutamate-gated chloride channel, said channel having the amino acid sequence of SEQ ID NO:14, and said channel being expressed in a host cell, a membrane preparation or an amphibian oocyte, said method comprising:

(a) applying glutamate to the host cell, membrane preparation or amphibian oocyte expressing said lepidopteran glutamate-gated chloride channel in the presence of chloride ions and measuring chloride flux; and (b) applying said agent and glutamate to a lepidopteran glutamate-gated chloride channel in the presence of chloride ions and measuring chloride flux;

(c) wherein a change in chloride flux in the presence of said agent is an indication that said agent modulates the activity of said lepidopteran glutamate-gated chloride channel.

* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide Primer mw 01
<221> NAME/KEY: variation
<222> LOCATION: (8)...(8)
<223> OTHER INFORMATION: n is a, t, g, or c
<221> NAME/KEY: variation
<222> LOCATION: (14)...(14)
<223> OTHER INFORMATION: n is a, t, g, or c

<400> SEQUENCE: 1
ggatgccnga yytnttytt                                              19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide Primer mw 02
<221> NAME/KEY: variation
<222> LOCATION: (3)...(3)
<223> OTHER INFORMATION: n is a, t, g, or c
<221> NAME/KEY: variation
<222> LOCATION: (12)...(12)
<223> OTHER INFORMATION: n is a, t, g, or c
<221> NAME/KEY: variation
<222> LOCATION: (15)...(15)
<223> OTHER INFORMATION: n is a, t, g, or c

<400> SEQUENCE: 2
tcnarccara answnaccc                                              19

<210> SEQ ID NO 3
<211> LENGTH: 451
<212> TYPE: DNA
<213> ORGANISM: Heliothis virescens

<400> SEQUENCE: 3
ggatgccgga tttgtttttc tccaacgaga aggaaggtca tttccacaac atcatcatgc    60
cgaacgtgta catccggatc ttccccaacg gcaacgtgct gtacagcatc cgaatctcct   120
tgacgctctc gtgccccatg aacctcaagt tgtaccccct ggataagcag acctgctcgc   180
tcaggatggc tagttatggt tggaccacag acgacttagt gttcctatgg aaggaaggcg   240
acccggtgca ggtggtgaag aacttacacc tgcctcggtt cacgctggag aagttcctca   300
ctgactactg caacagtaag actaataccg gtgaatacag ttgcctgaag gtagacttgc   360
tcttcaaacg cgagttcagt tactacctga tccagatcta cattccgtgc tgcatgctgg   420
tcatcgtgtc ctgggtcacc ttttggctcg a                                 451

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide Primer mw 03

<400> SEQUENCE: 4
cctgcaccgg gtcgccttcc ttcc                                         24

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide Adaptor Primer, AP1

<400> SEQUENCE: 5
ccatcctaat acgactcact atagggc                                27

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide Primer mw 04

<400> SEQUENCE: 6
tacagcatcc gaatctcctt gacgc                                  25

<210> SEQ ID NO 7
<211> LENGTH: 762
<212> TYPE: DNA
<213> ORGANISM: Heliothis virescens

<400> SEQUENCE: 7
cgctgagcat tgcgaactac gccttcaaca ttgttttttt aaacaagcac cgttttttaa      60
ttttaaaagc tctcattaaa ggttttattt gaaggaaagt tgtgacagca accggagtcg     120
tttagaatgg gactttgttg agtcagagga tggacatccc gcggccatca tgcgccctcg     180
tattggtgtt gttatttgtc acccatctct cagaatgcat gaacggtggg aagatcaact     240
tccgagagaa ggagaagcag atcctggatc agatcctggg ccccggggagg tacgacgcca     300
ggatcagacc ctcggggatc aacggcaccg atgggccagc ggtagtgagc gtcaatatat     360
ttgtccgaag tatatcaaag atcgatgatg tcacaatgga atactccgta cagttaacgt     420
tcgggaaca atggttagat gaacggctca aattcaataa tcttggaggt cgcctcaaat     480
acctgacgct taccgaagcc aacagagtct ggatgcctga tctattcttc tccaacgaga     540
aggaaggtca tttccacaac atcatcatgc cgaacgtgta catccgaatc ttccccaacg     600
gcaacgtgct gtacagcatc cgaatctccc tgacgctctc gtgccccatg aacctcaagt     660
tgtaccccct ggataagcag acctgctcgc tcaggatggc tagttatggt tggaccacag     720
acgacttagt gttcctatgg aaggaaggcg acccggtgca gg                        762

<210> SEQ ID NO 8
<211> LENGTH: 1052
<212> TYPE: DNA
<213> ORGANISM: Heliothis virescens

<400> SEQUENCE: 8
cgctctcgtg ccccatgaac ctcaagttgt acccctgga taagcagacc tgctcgctca      60
ggatggctag ttatggttgg accacagacg acttagtgtt cctatggaag gaaggcgacc     120
cggtgcaggt ggtgaaaaac ttacacctgc ctcggttcac gctggagaag ttcctcactg     180
actactgcaa cagtaagact aataccggtg aatacagttg cctgaaggta gacctgctct     240
tcaaacgcga gctcagttac tacctgatcc agatctacat tccgtgctgc atgctggtca     300
tcgtgtcctg ggtgtccttc tggctggacc agggagctgt gcctgcgagg gtctcactag     360
gagtgacgac tttacttaca atggcgaccc agtcgtcagg catcaacgcg tccctaccac     420

-continued

```
cggtgtccta cacgaaagcc attgatgtct ggactggtgt atgtctcaca ttcgtattcg      480
gagcgctact agagttcgcg ctcgtcaact atgcgtctcg ctctgacatg caccgagaga      540
acatgaagaa agcgagacgg gagatggaag cagccagcat ggatgctgcc tcagatctcc      600
ttgatacaga tagcaacacc acctttgcta tgaaacccttt ggtgcgcggc ggcgtggtgg      660
aatccaagat gcggcagtgc gagatccaca tcaccccgcc gcggaagaac tgctgccgcc      720
tgtggatgtc caagttcccc acgcgctcca agaggataga cgtcatctcc aggatcacct      780
tcccacttgt gttcgctctg tttaacctgg cttactgaat gaagcagaga aactcctcct      840
ttgcgcacag aaatcctgaa gagactgaac aacgaagttt cctaaccaca atcattgcta      900
tgattatacc gagaatttat tttatactaa ttgttgtgac cacacggttt taacgtagct      960
tggatccacg cggtgttaat atttgttgat cgcttagaat aaataaatat gctttgttga     1020
aaaaaaaaaa aaaaaaaaaa aaaaaaaaaa aa                                    1052
```

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide Gene Specific Primer 1 (GSP1)

<400> SEQUENCE: 9

```
gctgagcatt gcgaactacg ccttcaac                                          28
```

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide Gene Specific Primer 2 (GSP2)

<400> SEQUENCE: 10

```
taacaccgcg tggatccaag ctacg                                             25
```

<210> SEQ ID NO 11
<211> LENGTH: 1609
<212> TYPE: DNA
<213> ORGANISM: Artificial Sequence
<220> FEATURE:
<223> OTHER INFORMATION: PCR amplified fragment of Heliothis DNA cloned
      into pCR2.1-TOPO vector (Invitrogen)

<400> SEQUENCE: 11

```
ctgagcattg cgaactacgc cttcaacatt gtttctttaa acaaacaccg ttttttaatt       60
ttaatagcac tcattaaagg ttttatttga aggaaagttg tgacagcaac cggagtcgtt      120
tagaatggga ctttgttgag tcggaggatg acatcccgc ggccatcatg cgccctcgta       180
ttggtgttgt tatttgtcac ccatctctca gaatgcatga acgtgggaa gatcaacttt       240 cgagagaagg agaagcagat cctggatcag atcctgggcc ccgggaggta cgacgccagg      300
atcagaccct cggggatcaa cggcactgat gggccagcgg tagtgagcgt caatatattt      360
gtccgaagta tatcaaagat cgatgacgtc acaatggaat actccgtaca attaacgttt      420
cgggaacaat ggttagatga acggctcaaa ttcaataatc ttggaggtcg cctcaaatac      480
ctgacactga ctgaagccaa cagagtctgg atgcctgatc tattcttctc caacgagaag      540
gaaggtcatt tccacaacat catcatgccg aacgtgtaca tccgaatctt ccccaacggc      600
aacgtgctgt acagcatccg aatctccctg acgctctcgt gccccatgaa cctcaagttg      660
```

```
taccccctgg ataagcagac ctgctcgctc aggatggcta gttatggttg gaccacagac      720
gacttagtgt tcctatggaa ggaaggcgac ccggtgcagg tggtgaaaaa cttacacctg      780
cctcggttca cgctggagaa gttcctcact gactactgca acagtaagac taataccggt      840
gaatacagtt gcctgaaggt agacctgctc ttcaaacgcg agttcagtta ctacctgatc      900
cagatctaca ttccgtgctg catgctggtc atcgtgtcct gggtgtcctt ctggctggac      960
cagggagctg tgcctgcgag ggtctcacta ggagtgacga ctttacttac aatggcgacc     1020
cagtcgtcag gcatcaacgc gtccctacca ccggtgtcct acacgaaagc cattgatgtc     1080
tggactgggt tatgtctcac attcgtattc ggagcgctac tagagtttgc gctcgtcaac     1140
tatgcgtctc gctctgacat gcaccgagag aacatgaaga agcgagacg ggagatggaa      1200 gcagccagca tggatgctgc ctcagatctc cttgatacag atagcaacac caccttgct       1260 atgaaaccct tggtgcgcgg cggcgtggtg gaatccaaga tgcggcagtg cgagatccac     1320
atcaccccgc cgcggaagaa ctgctgccgc ctgtggatgt ccaagttccc cacgcgctcc     1380
aagaggatag acgtcatctc caggatcacc ttcccacttg tgttcgctct gtttaacctg     1440
gcttactgaa tgaagcagag aaactcctcc tttgcgcaca gaaatcctga agagactgaa     1500
caacgaagtt tcctaaccac aatcattgct atgattatac cgagaattta ttttatacta     1560
attgttgtga ccacacggtt ttaacgtagc ttggatccac gcggtgtta                  1609
```

<210> SEQ ID NO 12
<211> LENGTH: 1640
<212> TYPE: DNA
<213> ORGANISM: Artificial Sequence
<220> FEATURE:
<223> OTHER INFORMATION: PCR amplified fragment of Heliothis DNA cloned
      into pCR2.1-TOPO vector (Invitrogen)

<400> SEQUENCE: 12

```
aggtgcggac gtctgcactt gcgaatcgaa gtgatagaaa atagttcgat gaatacggga       60
gtttgagtgg agtgatttat aattcggagg atggacatcc cgcggccatc atgcgccctc      120
gtattggtgt tgttatttgt cacccatctc tcagaatgca tgaacggtgg gaagatcaac      180
tttcgagaga aggagaagca gatcctggat cagatcctgg gccccgggag gtacgacgcc      240
aggatcagac cctcggggat caacggcact ggctatgcgc aacgttagt ccatgtcaac       300 atgtatctac ggtccatcag caaaatagat gattacaaaa tggaatactc cgtacaatta      360
acgtttcggg aacaatggtt agatgaacgg ctcaaattca ataatcttgg aggtcgcctc      420
aaatacctga cactgactga agccaacaga gtctggatgc ctgatctatt cttctccaac      480
gagaaggaag gtcatttcca caacatcatc atgccgaacg tgtacatccg gatcttcccc      540
aacggcaacg tgctgtacag catccgaatc tccctgacgc ctcgtgccc catgaacctc       600 aagttgtacc cctggataa gcagacctgc tcgctcagga tggctagtta tggttggacc       660
acagacgact agtgttcct atggaaggaa ggcgacccgg tgcaggtggt gaaaaactta      720
cacctgcctc ggttcacgct ggagaagttc ctcactgact actgcaacag taagactaat     780
accggtgaat acagttgcct gaaggtagac ctgctcttca aacgcgagtt cagttactac     840
ctgatccaga tctacattcc gtgctgcatg ctggtcatcg tgtcctgggt gtccttctgg      900
ctggaccagg gagctgtgcc tgcgagggtc tcactaggag tgacgacttt acttacaatg      960
gcgacccagt cgtcaggcat caacgcgtcc ctaccaccgg tgtcctacac gaaagccatt     1020
gatgtctgga ctgggttatg tctcacattc gtattcggag cgctactaga gtttgcgctc     1080
```

-continued

```
gtcaactatg cgtctcgctc tgacatgcac cgagagaaca tgaagaaagc gagacgggag   1140
atggaagcag ccagcatgga tgctgcctca gatctccttg atacagatag caacaccacc   1200
tttgctatga aacccttggt gcgcggcggc gtggtggaat ccaagatgcg gcagtgcgag   1260
atccacatca ccccgccgcg gaagaactgc tgccgcctgt ggatgtccaa gttccccacg   1320
cgctccaaga ggatagacgt catctccagg atcaccttcc cacttgtgtt cgctctgttt   1380
aacctggctt actgttgggg gggcaagagg ggggcggtgg ctgctaccat gtcttgcagg   1440
agcgatgaga ctattaatgc tatttataag ctgatacaga atgaagcaga gaaactcctc   1500
ctttgcgcac agaaatcctg aagagactga acaacgaagt ttcctaacca caatcattgc   1560
tatgattata ccgagaattt attttatact aattgttgtg accacacggt tttaagctag   1620
cttggatcca cgcggtgtta                                                1640
```
<210> SEQ ID NO 13
<211> LENGTH: 4621
<212> TYPE: DNA
<213> ORGANISM: Heliothis virescens
<220> FEATURE:
<221> NAME/KEY: unsure
<222> LOCATION: (764)...(764)
<223> OTHER INFORMATION: n is a, t, g, or c

<400> SEQUENCE: 13

```
accaggcgaa ctacgccttc aacattgttt ttttaaacaa acaccgtttt ttaattttaa     60
tagctctcat taaaggtttt atttgaagga aagttgtgac agcaaccgga gtcgtttaga    120
atgggacttt gttgagtcgg aggatggaca tcccgcggcc atcatgcgcc ctcgtattgg    180
tgttgttatt tgtcacccat ctctcagaat gcatgaacgg tgggaagatc aactttcgag    240
agaaggagaa gcagatcctg gatcagatcc tgggccccgg gaggtacgac gccaggatca    300
gaccctcggg gatcaacggc actgatgggc cagcggtagt gagcgtcaat atatttgtcc    360
gaagtatatc aaagatcgat gacgtcacaa tggaatactc cgtacagtta acgtttcggg    420
aacaatggtt agatgaacgg ctcaaattca ataatcttgg aggtcgcctc aaatacctga    480
cactgaccga agccaacaga gtctggatgc ctgatctatt cttctccaac gagaaggaag    540
gtcatttcca caacatcatc atgccgaacg tgtacatccg gatcttcccc aacggcaacg    600
tgctgtacag catccgaatc tccttgacgc tctcgtgccc catgaacctc aagttgtacc    660
ccctggataa gcagacctgc tcgctcagga tggctagtta tggttggacc acagacgact    720
tagtgttcct atggaaggaa ggcgacccgg tgcaggtggt gaanaactta cacctgcctc    780
ggttcacgct ggagaagttc ctcactgact actgcaacag taagactaat accggtgaat    840
acagttgcct gaaggtagac ttgctcttca aacgcgagtt cagttactac ctgatccaga    900
tctacattcc gtgctgcatg ctggtcatcg tgtcctgggt gtccttctgg ctggaccagg    960
gagctgtgcc tgcgagggtc tcactaggag tgacgacttt acttacaatg gcgacccagt   1020
cgtcaggcat caacgcgtcc ctaccaccgg tgtcctacac gaaagccatt gacgtctgga   1080
ctggtgtatg tctcacattc gtattcggag cgctactaga gttcgcgctc gtcaactatg   1140
cgtctcgctc tgacatgcac cgagagaaca tgaagaaagc gagacgggag atggaagcag   1200
ccagcatgga tgctgcctca gatctcctag acacagatag caacaccacc tttgctatga   1260
aacccttggt gcgcggcggc gtggtggaat ccaagatgcg gcagtgcgag atccacatca   1320
ccccgccgcg gaagaactgc tgccgcctgt ggatgtccaa gttccccacg cgctccaaga   1380
```

```
ggatagacgt catctccagg atcaccttcc cacttgtgtt cgctctgttt aacctggctt    1440
actggtcgac gtacctgttc cgcgacgagg acgaggagaa gtgattctcc gagtccctgg    1500 agagggcgt ggggccgcgc gtgcagctgg tggcggccgt cgtgatgccc tacgtgctgt    1560
tcgtggtggc gtactcgctg tgcttccgcg cgcgcgcccc gccccttcg ccccgcccg     1620 cgcccgcgcc cgcgcccgcg cccgcaccct cccgccgcag cgcgcgcgca cgcacacaag    1680
cacacccacc tagcccgctc tagcgaactc accccattca ttatcgtgac atattatatt    1740
atcgtgtatt ttaatcgacg tcttcctcgt ggcagcgtta ttcccactca gtattcgatg    1800
gcgttagtgt aattagtaaa gctcaagtgt ctatttgtat atatatgtga ccccgtgcc     1860 agtttagacc aagcctccgt ttttaaattg aagcagttcg agaaaaacgg taaaaataga    1920
ctcaattttg attggtcatc taaacagcag aactttttatt cggcacttat aaagtcctca    1980
attatttgtg tacaaaaata aatattttac tttccgagaa ttaaaaattt tcgataattt    2040
taccaatgat atgactcctt gtatggattc gtatgtaatg taaacctagg ttaagatata    2100
agaggaatcc cagaggttcc cgcatattac tttagccttt aaagtaaggt aaataaggac    2160
tagaatggca ctaatgtgta gtggaagtgg ggtattattt agtagttttc actctacagt    2220
acgtgaactg gactagatct actagcaaat agagttgatc aattttcatg tcgaaatgtt    2280
cacagatatt gtataaaccg ctggaggtaa acagctatca acaatgtaac accaaatacc    2340
atcagaatca agcaaaacca tggaaatttt gctaatcgaa aagttgtaac tgtttatcta    2400
tggcaggtat aattggccta gtaatgtatc gtgtagtatc atttacaaca catattaact    2460
attaaccaca ttatgtgaaa gaaggaattt ataaaaaaaa ccttattaaa tatatattag    2520
ataagtatta ttaattggat attctcttgc tggggatttt aatatgaatc ttacctttaa    2580
ataagtttga tctcactaga cgttgcaaat ggatacccca aatacctttt ccgcattaaa    2640
aggtattatt ttaacaaatg tattcttccc cgtcaatgtt ttaagactac gtatctacat    2700
aaaatgatgt attgttcata caatactatt tcaaaatgca agaacaacgt aaagtgcatt    2760
tcattgatgt ttgtgtatgt agatgacatt agtattttac ccaaaaatac tgatattaaa    2820
attcccagta agattcgtag gtaaatggta aacgtgtaaa tagttgggcc tacaactttc    2880
tacacctgtg tcgctcagtg tacagttacc tatatttaat attacaatta tatcattatt    2940
aacgaatgat aagattttat taacattaat ttctctgtct gaacgtatca ctgtaaatat    3000
tactaaatgt ttcctaatta cattattcat acatatatta tcatcccttg agctatagtt    3060
gcaaagtatt ccaaaaccac aatgaaaata aaatttcaat ttacttcacg atcaccaaat    3120
tgtgaaaacc tggttgttct gaattcattt aacaattagt ttttactttg aatccatggc    3180
tcaagggaca tcctaaggat attcattgaa atctatttag aatctcgtgt atgtatcatg    3240
acaccttcaa ataaaatatc actaatgctg tgttcggcta ttagatacaa taagtcgtac    3300
atattaacgt aagcacattc gttttttatta tgcggcggag agaacgcatc tgtttctata    3360
acgaaagggt ggccattatc ggctatatca tcttgcttgg tctgtataaa ataagagtc    3420 aaagactcgg gggaaacccc tatatgtata ctatcataac cgttatcctt attttgacaa    3480
agctctggga aacgaaatag cattttgttt caattacaca attcttgctc attttctct    3540 tccgcctttt atttgaattt aggtgttgcc cactgtgcgc aatactctaa tggcttagaa    3600
ttatccttaa tatatattct cgggctgtga cgaggtgtag catctgcatt attatattaa    3660
tgtcatttcg tttgccattc gttgtatgta aggaaatatt agcctatgtc caacgctcaa    3720
aatctcatag acgtattagg cacacataag tgtacctttt cgtatgtatg taaattattg    3780
```

-continued

```
gagactcaat gtcttagttg gtgctatata tactacgatc cgaggagaat gtacccagta    3840
gtttactcat acataacgcc actgatatct tgtggaggaa atattatctg cgagacaagt    3900
agacattagt taagtttaca tatttacaat aaatgtttcc attattagga tataacatat    3960
gaatgtgtta ctgttgaaag cagcttctca aggtaccacc agtaattcgg agatacttgt    4020
aggatttgca ttcgataaac aacttatact aaaacgaaga tttgactgaa tctaaaccgc    4080
aaatactgtg gtcaaaatta ttaaacactt tcaatacatg ttgtacgcat gtttctgtaa    4140
tttcacattt aattgtaaag tcaattaaat cactgtataa taatacattt tcaacatatc    4200
tctcactgtt aagatttcgg ttggtccaac gacagaatca aatcgcaacg taatgatgat    4260
ccgggcaaaa ctaacaacta gatagatctc ttaaatgatt acgttgaagt ggaagaggtg    4320
atgtatgaag gaaggtagga ttaagtaaca ctgtataata tattgaccat aattacgatt    4380
ttagaagtca taatgacgg tttacctctt aagattatac agtaaaggta gatagtttca    4440
ttcgtaagct atgttgtact cgattggtat gacataacta atgactgagc tttgtcatct    4500
actacaaccc gagggcgaat acctccttct tctaccattc ccatttaatt ataaagaaac    4560
attgtaaaaa atgatttaat aaaatatccc aaatatctta aacaaaaaa aaaaaaaaa    4620 a                                                                   4621
```

<210> SEQ ID NO 14
<211> LENGTH: 450
<212> TYPE: PRT
<213> ORGANISM: Heliothis virescens

<400> SEQUENCE: 14

```
Ser Glu Gln Ile Asp Asn Met Asp Ile Pro Arg Pro Ser Cys Ala Leu
  1               5                  10                  15

Val Leu Leu Phe Val Thr His Leu Ser Glu Cys Met Asn Gly Gly Lys
             20                  25                  30

Ile Asn Phe Arg Glu Lys Glu Lys Gln Ile Leu Asp Gln Ile Leu Gly
         35                  40                  45

Pro Gly Arg Tyr Asp Ala Arg Ile Arg Pro Ser Gly Ile Asn Gly Thr
     50                  55                  60

Asp Gly Pro Ala Val Val Ser Val Asn Ile Phe Val Arg Ser Ile Ser
 65                  70                  75                  80

Lys Ile Asp Asp Val Thr Met Glu Tyr Ser Val Gln Leu Thr Phe Arg
                 85                  90                  95

Glu Gln Trp Leu Asp Glu Arg Leu Lys Phe Asn Asn Leu Gly Gly Arg
            100                 105                 110

Leu Lys Tyr Leu Thr Leu Thr Glu Ala Asn Arg Val Trp Met Pro Asp
        115                 120                 125

Leu Phe Phe Ser Asn Glu Lys Glu Gly His Phe His Asn Ile Ile Met
    130                 135                 140

Pro Asn Val Tyr Ile Arg Ile Phe Pro Asn Gly Asn Val Leu Tyr Ser
145                 150                 155                 160

Ile Arg Ile Ser Leu Thr Leu Ser Cys Pro Met Asn Leu Lys Leu Tyr
                165                 170                 175

Pro Leu Asp Lys Gln Thr Cys Ser Leu Arg Met Ala Ser Tyr Gly Trp
            180                 185                 190

Thr Thr Asp Asp Leu Val Phe Leu Trp Lys Glu Gly Asp Pro Val Gln
        195                 200                 205

Val Val Lys Asn Leu His Leu Pro Arg Phe Thr Leu Glu Lys Phe Leu
```

-continued

```
            210                 215                 220
Thr Asp Tyr Cys Asn Ser Lys Thr Asn Thr Gly Glu Tyr Ser Cys Leu
225                 230                 235                 240

Lys Val Asp Leu Leu Phe Lys Arg Glu Phe Ser Tyr Tyr Leu Ile Gln
                245                 250                 255

Ile Tyr Ile Pro Cys Cys Met Leu Val Ile Val Ser Trp Val Ser Phe
                260                 265                 270

Trp Leu Asp Gln Gly Ala Val Pro Ala Arg Val Leu Leu Gly Val Thr
            275                 280                 285

Thr Leu Leu Thr Met Ala Thr Gln Ser Ser Gly Ile Asn Ala Ser Leu
    290                 295                 300

Pro Pro Val Ser Tyr Thr Lys Ala Ile Asp Val Trp Thr Gly Val Cys
305                 310                 315                 320

Leu Thr Phe Val Phe Gly Ala Leu Leu Glu Ser Arg Phe Val Asn Tyr
                325                 330                 335

Ala Ser Arg Ser Asp Met His Arg Glu Asn Met Lys Lys Ala Arg Arg
            340                 345                 350

Glu Met Glu Ala Ala Ser Met Asp Ala Ala Ser Asp Leu Leu Asp Thr
        355                 360                 365

Asp Ser Asn Thr Thr Phe Ala Met Lys Pro Leu Val Arg Gly Gly Val
    370                 375                 380

Val Glu Ser Lys Met Arg Gln Cys Glu Ile His Ile Thr Pro Pro Arg
385                 390                 395                 400

Lys Asn Cys Cys Arg Leu Trp Met Ser Lys Phe Pro Thr Arg Ser Lys
                405                 410                 415

Arg Ile Asp Val Ile Ser Arg Ile Thr Phe Pro Leu Val Phe Ala Leu
                420                 425                 430

Phe Asn Leu Ala Tyr Trp Ser Thr Tyr Leu Phe Arg Asp Glu Asp Glu
            435                 440                 445

Glu Lys
    450
```